(12) United States Patent
Riquelme et al.

(10) Patent No.: US 7,338,935 B2
(45) Date of Patent: Mar. 4, 2008

(54) CHROMATOGRAPHIC SEPARATION OF THERAPEUTIC POLYPEPTIDES

(75) Inventors: Patricio T. Riquelme, Emeryville, CA (US); Corazon Terciano Victa, Emeryville, CA (US); Walter Joseph Crosier, Emeryville, CA (US); John Tharin Wendell, Emeryville, CA (US)

(73) Assignee: Chiron Corporation, Emeryville, CA (US)

( * ) Notice: Subject to any disclaimer, the term of this patent is extended or adjusted under 35 U.S.C. 154(b) by 22 days.

(21) Appl. No.: 10/939,239

(22) Filed: Sep. 9, 2004

(65) Prior Publication Data

US 2005/0131213 A1    Jun. 16, 2005

Related U.S. Application Data

(60) Provisional application No. 60/501,610, filed on Sep. 9, 2003.

(51) Int. Cl.
 *A61K 38/16* (2006.01)
 *A61K 38/00* (2006.01)
 *A23J 1/00* (2006.01)

(52) U.S. Cl. .......................... 514/12; 530/324; 530/417

(58) Field of Classification Search ...................... None
 See application file for complete search history.

(56) References Cited

OTHER PUBLICATIONS

Gel Filtration, Principles and Methods, Amersham Biosciences, Last Modified, Aug. 9, 2002.*
Pasechnik, Journal of Chromatography, (1986), 364, 359-368.*
Knuth, et al., Protein Purification: Micro to Macro, 1987, Alan r. Liss, Inc., 279-305.*
Konishi, 1985, Progress in HPLC, 1, 43-57.*
Blank, et al., Eur. J. Biochem., 267, 5711-5716.*
The Handbook of Gel Filtration, Amersham Biosciences.*
Majors, R. E., LCGC 2001, 19(2), 124, 126,128, 130.*
Russell-Harde et al., "The Use of Zwittergent 3-14 in the Purification of Recombinant Human Interferon-β $Ser^{17}$ (Beta seron)" *J. Interferon and Cytokine Research* 15:31-37, 1995.
Runkel et al., "Structural and Functional Differences Between Glycosylated and Non-glycosylated Forms of Human Interferon-β (IFN-β)" *Pharmaceutical Research* 15(4):641-649, 1998.
Helenius et al., "Properties of Detergents" *Methods in Enzymology* 56:734-749, 1979.
Turro and Lei, "Spectroscopic Probe Analysis of Protein-Surfactant Interactions: The BSA/SDS System" *Langmuir* 11:2525-2533, 1995.
Steele et al., "Molecular Weight and Hydrodynamic Properties of Apolipoprotein B in Guanidine Hydrochloride and Sodium Dodecyl Sulfate Solutions" 254(5):1639-1643, 1979.
Takeda et al., "The Interaction of Bovine Serum Albuimin with Sodium Dodecyl Sulfate: Binding of the Surfactant and Conformational Change of the Protein Induced by the Binding" *Curr. Top. Colloid Interface Sci.* 1:109-135, 1997.

* cited by examiner

*Primary Examiner*—Anish Gupta
*Assistant Examiner*—Satyanarayana R. Gudibande
(74) *Attorney, Agent, or Firm*—Denise S. Bergin; Alisa A. Harbin

(57) ABSTRACT

The present invention is directed to the purification and commercialization of therapeutic polypeptides that have. In one aspect of the invention, a method of purifying Interferon β-1b using size exclusion chromatography is provided. In another aspect of the invention, a method of purifying a polypeptide using size chromatography is provided. A third aspect provides a method of commercializing a polypeptide.

32 Claims, 11 Drawing Sheets

CHROMATOGRAPHIC SEPARATION OF THERAPEUTIC POLYPEPTIDES

CROSS-REFERENCE TO RELATED APPLICATIONS

This application claims the benefit of U.S. patent application No. 60/501,610, filed Sep. 9, 2003. The disclosure of the above provisional application is herein incorporated by reference in its entirety and for all purposes as if fully set forth herein.

BACKGROUND OF THE INVENTION

1. Field of the Invention

The present invention is directed to the purification and commercialization of polypeptides that have demonstrated therapeutic value.

2. State of the Art

REFERENCES

The following literature publications are cited in this section. All of the identified publications are herein incorporated by reference in their entirety to the same extent as if each individual publication was specifically and individually incorporated by reference in its entirety.

Helenius, A., McCaslin, D. R., Fries, E. and Tanford, C. in "Properties of Detergents" Methods in Enzymology, vol. 56 (1979), Pages 734-749.

Turro, N. J., Lei, X., Ananthapadmanabhan, K. P. and Aronson, M. in "Spectroscopic probe analysis of protein-surfactant interactions: the BSA/SDS system" Langmuir (1995), vol. 11, Pages 2525-2533.

There are many therapeutically important polypeptides currently marketed for the treatment of a disease. Interferons, for instance, are important cytokines that exhibit antiviral, antiproliferative and immunomodulatory activities. Such activities have been used to derive clinical benefits from the polypeptides for a number of disease states, such as hepatitis, various cancers and multiple sclerosis. The interferons are classified as being of two different types—type I and type II. Interferons $\alpha$, $\beta$, $\tau$ and $\omega$ are members of type I interferons, while interferon $\gamma$ is the only known member of the distinct type II class.

Human Interferon $\beta$ consists of 166 amino acid residues and has a molecular weight of approximately 22 kDa. It is produced by most cells in the body, but particularly by fibroblasts in response to a viral infection or other biological invader. The binding target of Interferon $\beta$ is a multimeric cell surface receptor, which, upon binding, activates a cascade of intracellular events leading to the expression of antiviral, antiproliferative and immunomodulatory characteristics.

A variety of different techniques have been used to characterized the structure of human Interferon $\beta$. For instance, the amino acid sequence of human interferon has been reported (see Taniguchi, *Gene* 10:11-15, 1980), as well as crystal structures for both human and murine Interferon $\beta$ (see respectively, *Proc. Natl. Acad. Sci. USA* 94:11813-11818, 1997. *J. Mol. Biol.* 253:187-207, 1995). Such structural data has also been the subject of a review article. (See, *Cell Mol. Life Sci.* 54:1203-1206, 1998.)

Preparations of Interferon $\beta$ are sold under the tradenames BETASERON®, AVONEX™, and REBIF®. BETASERON® is also known as Interferon $\beta$-$1_b$, which is a non-glycosylated protein having a deletion of an N-terminal methionine. Interferon $\beta$-$1_b$ is a mutein in which the cystein at position 17 has been mutated to a serine. It is produced using recombinant bacterial cells. AVONEX™ and REBIF®, which are different commercial forms of Interferon $\beta$-$1_a$, are glycosylated and produced using recombinant mammalian cells. Interferon $\beta$-$1_a$ does not contain a mutation at amino acid position 17. These agents are used to treat patients with multiple sclerosis, and have been shown to be effective in reducing the exacerbation rate of the disease.

Interferon $\beta$ has been shown to delay the progression of multiple sclerosis and to be effective in the treatment of a variety of other diseases. Its mechanism of action for delaying multiple sclerosis remains largely unclear. Some activities that may act in concert to account for the compound's therapeutic effect, however, include the following: Interferon $\beta$ has inhibitory effects on the proliferation of leukocytes and antigen presentation and may modulate the profile of cytokine production towards an anti-inflammatory phenotype; and, Interferon $\beta$, through the inhibition of T-cell matrix metalloproteases, can reduce T-cell migration. (See, *Neurol.* 51:682-689, 1998.) Other diseases that Interferon $\beta$ may be used to treat include osteosarcoma, basal cell carcinoma, cervical dysplasia, glioma, acute myeloid leukemia, multiple myeloma, Hodgkin's disease, breast carcinoma, melanoma, and viral infections such as papilloma virus, viral hepatitis, herpes genitalis, herpes zoster, herpetic keratitis, herpes simplex, viral encephalitis, cytomegalovirus pneumonia, and rhinovirus.

Given Interferon $\beta$'s therapeutic importance, it is crucial to obtain commercial preparations of the polypeptide in an economical and efficient way. Recombinant methods of Interferon $\beta$ preparation yield substantial amounts of the compound, but that is only the first step. After production, Interferon $\beta$ must be isolated and purified to an extent that is medically acceptable. Such purification of the polypeptide, and other polypeptides like it, is an object of the subject invention.

SUMMARY OF THE INVENTION

The present invention is directed to the purification and commercialization of polypeptides that have therapeutic value.

In a method aspect of the invention, a method of purifying Interferon $\beta$-$1_b$ using size exclusion chromatography is provided. In this method, a buffering solution is prepared. The buffering solution comprises greater than 50 mM salt and less than 500 mM salt. Interferon $\beta$-$1_b$ is loaded onto a size exclusion chromatography column. Interferon $\beta$-$1_b$ is preferably loaded onto the column using the buffering solution. When Interferon $\beta$-$1_b$ is loaded using a buffering solution, a mixture comprising Interferon $\beta$-$1_b$ and the buffering solution can be prepared. Interferon $\beta$-$1_b$ is passed through a column containing a polymeric gel, and elution fractions containing purified Interferon $\beta$-$1_b$ and buffering solution are collected. During elution of Interferon $\beta$-$1_b$, an elution profile is observed and an asymmetry value of the elution profile is determined. Elution fractions are collected when the asymmetry value of an elution profile is between 0.1 and 2.0. Preferably, elution fractions are collected when the asymmetry value of the elution profile is between 0.2 and 1.9, between 0.3 and 1.8, 0.4 and 1.7, 0.4 and 1.6, and 0.5 and 1.5. Even more preferably, elution fractions are collected when the asymmetry value of the elution profile is between 0.8 and 1.2 or between 0.9 and 1.1.

Any desired amount of Interferon β-1$_b$ is purified using the method. Typical amounts, however, are greater than 1.0 g, 2.5 g, 5.0 g, 10 g, 25 g, 50 g, 100 g, 150 g, 200 g, 250 g, or 300 g.

This method provides purified polypeptide wherein the amount of a contaminating polypeptide (e.g., a host protein when the desired polypeptide is recombinantly produced) is present at a concentration of less than 1 µg per 1 mg of the desired polypeptide. Preferably, the amount of contaminating polypeptide is present at a concentration of less than 500 ng per 1 mg of the desired polypeptide, less than 250 ng per 1 mg of the desired polypeptide, 100 ng per 1 mg of the desired polypeptide, 75 ng per 1 mg of the desired polypeptide. Even more preferably, the amount of contaminating polypeptide is present at a concentration of less than 50 ng per 1 mg of the desired polypeptide, 25 ng per 1 mg of the desired polypeptide, and 10 ng per 1 mg of the desired polypeptide.

The polymeric gel is of any suitable composition. Typically, the gel is selected from a group of gels including dextran (i.e., SEPHADEX®), agarose (i.e., SEPHAROSE®), and polyacrylamide (SEPHACRYL®). A gel that is oftentimes used is Sephadex G75 SF, which is a dextran-based gel having a dry particle diameter of 10 to 40 µm.

The volume of the column containing the polymeric gel is typically less than 450 cm$^3$. Oftentimes, the volume is less than 400 cm$^3$, 350 cm$^3$, or 300 cm$^3$.

The salt of the buffering solution can be any salt useful in size exclusion chromatography. The salts useful in the invention include salts of acetate, phosphate, pyrophosphate, bicarbonate, carbonate, borate, citrate, formate, succinate, oxalate, tartarate, maleate, arseniate, histidine, MES, ADA, Pipes, tris, ethylendiamine, BES, MOPS, TES, Hepes, triethanolamine, EPPS, tricine, glycylglycine, bicine, ammonia, chloride, sulfate, fluoride, iodide, bromide, trifluoroacetate, and trichloroacetate. Typically, the ionic strength of the buffering solution is greater than 75 mM salt and less than 250 mM salt, or greater than 100 mM salt and less than 200 mM salt, or about 150 mM salt. Preferably, the ionic strength of the buffering solution is around, 50 mM salt, 75 mM salt, 100 mM salt, 125 mM salt, 150 mM salt, 175 mM salt, 200 mM salt, 225 mM salt, or 250 mM salt. The pH of the buffering solution can be any pH useful in the purifying therapeutic polypeptides in size exclusion chromatography. Typically, the pH of the buffering solution is between about 3 and about 10. Preferably, the pH is between about 4 and about 9, between about 5 and about 8, between about 5 and about 7, between about 6 and 7, or between 7 and 8.

The salt of the buffering solution is oftentimes an acetate. Typically, the ionic strength of the buffering solution contains greater than 75 mM acetate and less than 250 mM acetate, or greater than 100 mM acetate and less than 200 mM acetate, or about 150 mM acetate. Preferably, the ionic strength of the buffering solution is around, 50 mM acetate, 75 mM acetate, 100 mM acetate, 125 mM acetate, 150 mM acetate, 175 mM acetate, 200 mM acetate, 225 mM acetate, or 250 mM acetate. Any suitable acetate may be used, including lithium acetate, sodium acetate, potassium acetate, and acetates of protonated organic amines such as tris, triethylamine, and piperidine.

Typically, the buffering solution contains an ionic detergent. Examples of such detergents include, without limitation, sodium dodecyl sulfate (i.e., "SDS"), cetyltrimethyl ammonium bromide, lysolecithin, ether deoxylysolecithin, sodium cholate, sodium taurodeoxycholate, alkyl sulphonates, alkyl arylsulphonates, alkyl sulfates, alkyl arylsulfates, alkyl sarcosidates, cationic alkylamines, quaternary amines, and alkylpyridinium derivatives. Any soluble salt of the ionic detergent can be used, for example, sodium dodecyl sulfate. When present, the detergent is typically at a concentration between 0.05 weight percent and 0.25 weight percent. Oftentimes, it is present at a concentration between 0.075 weight percent and 0.2 weight percent, or at about 0.1 weight percent.

Oftentimes, the buffering solution contains a metal chelator. Typically, ethylenediaminetetraacetic acid is used, but any suitable metal chelator may be used. Metal chelator concentrations within the buffering solution are typically between 0.5 mM and 1.5 mM, 0.75 mM to 1.25 mM, or about 1 mM.

The step of collecting elution fractions typically includes observing an elution profile during size exclusion chromatography. When Interferon β-1$_b$ is exiting the column, its presence in an elution fraction is determined usually by observing the optical absorbance of the elution fractions at 280 nm. The absorbance values of each of the fractions are used to prepare an elution profile.

An asymmetry value of the elution profile is calculated. The asymmetry value is a ratio of width from a tailing half of the peak to a width of a leading half of the peak measured at ten percent of peak height. Elution fractions containing Interferon β-1$_b$ are collected when the asymmetry value of the elution profile is between 0.4 and 1.6. Oftentimes elution fractions containing Interferon β-1$_b$ are collected when the asymmetry value of the elution profile is between 0.5 and 1.5, 0.6 and 1.4, 0.7 and 1.3, 0.8 and 1.2, or 0.9 and 1.1.

Methods of monitoring the presence of Interferon β-1$_b$ in an elution fraction include, without limitation, observing the absorbance of the elution fraction at $A_{280}$, conductivity measurements and analysis by SDS-PAGE.

It typically takes less than 48 hours for the mixture comprising Interferon β-1$_b$ to pass through the column. Oftentimes, it takes less than 40, 35, 30, 25, 20, 15, 10, 5, or 3 hours.

In another method aspect of the invention, a method of purifying a polypeptide using size exclusion chromatography is provided. In this method, a buffering solution is prepared. The buffering solution includes greater than 50 mM salt and less than 500 mM salt. The polypeptide is loaded onto size exclusion chromatography column. The polypeptide is preferably loaded onto a column using the buffering solution. When the polyptptide is loaded using the buffering solution, a mixture comprising the polypeptide and a buffering solution can be prepared. The polypeptide is passed through a column containing a polymeric gel, and elution fractions containing purified polypeptide and buffering solution are collected. During elution of the polypeptide, an elution profile is observed and an asymmetry value of the elution profile is determined. Elution fractions are collected when the asymmetry value of an elution profile is between 0.1 and 2.0. Preferably, elution fractions are collected when the asymmetry value of the elution profile is between 0.2 and 1.9, between 0.3 and 1.8, 0.4 and 1.7, 0.4 and 1.6, and 0.5 and 1.5. Even more preferably, elution fractions are collected when the asymmetry value of the elution profile is between 0.8 and 1.2 or between 0.9 and 1.1.

Nonlimiting examples of polypeptides purified by the method include any therapeutically useful polypeptide including monoclonal antibodies, interferons (e.g., IFN β, IFN β-1$_a$, and IFN β-1$_b$), interleukins (e.g., IL-2), Filgrastin, and Epoietin-α.

Any desired amount of Interferon polypeptide is purified using the method. Typical amounts, however, are greater than 1.0 g, 2.5 g, 5.0 g, 10 g, 25 g, 50 g, 100 g, 150 g, 200 g, 250 g, or 300 g.

This method provides purified polypeptide wherein the amount of a contaminating polypeptide (e.g., E. coli protein when IFN β-$1_b$ is recombinantly produced) is present at a concentration of less than 1 μg per 1 mg of the desired polypeptide. Preferably, the amount of contaminating polypeptide is present at a concentration of less than 500 ng per 1 mg of the desired polypeptide, less than 250 ng per 1 mg of the desired polypeptide, 100 ng per 1 mg of the desired polypeptide, 75 ng per 1 mg of the desired polypeptide. Even more preferably, the amount of contaminating polypeptide is present at a concentration of less than 50 ng per 1 mg of the desired polypeptide, 25 ng per 1 mg of the desired polypeptide, and 10 ng per 1 mg of the desired polypeptide.

The polymeric gel is of any suitable composition. Typically, the gel is selected from a group of gels including dextran (i.e., SEPHADEX®), agarose (i.e., SEPHAROSE®), and polyacrylamide (SEPHACRYL®). A gel that is oftentimes used is Sephadex G75 SF, which is a dextran-based gel having a dry particle diameter of 10 to 40 μm.

The volume of the column containing the polymeric gel is typically less than 450 cm$^3$. Oftentimes, the volume is less than 400 cm$^3$, 350 cm$^3$, or 300 cm$^3$.

The salt of the buffering solution can be any salt useful in size exclusion chromatography. The salts useful in the invention include salts of acetate, phosphate, pyrophosphate, bicarbonate, carbonate, borate, citrate, formate, succinate, oxalate, tartarate, maleate, arseniate, histidine, MES, ADA, Pipes, tris, ethylendiamine, BES, MOPS, TES, Hepes, triethanolamine, EPPS, tricine, glycylglycine, bicine, ammonia, chloride, sulfate, fluoride, iodide, bromide, trifluoroacetate, and trichloroacetate. Typically, the ionic strength of the buffering solution is greater than 75 mM salt and less than 250 mM salt, or greater than 100 mM salt and less than 200 mM salt, or about 150 mM salt. Preferably, the ionic strength of the buffering solution is around, 50 mM salt, 75 mM salt, 100 mM salt, 125 mM salt, 150 mM salt, 175 mM salt, 200 mM salt, 225 mM salt, or 250 mM salt. Typically, the pH of the buffering solution is between about 3 and about 10. Preferably, the pH is between about 4 and about 9, between about 5 and about 8, between about 5 and about 7, between about 6 and 7, or between 7 and 8.

The salt of the buffering solution is oftentimes an acetate. Typically, the ionic strength of the buffering solution contains greater than 75 mM acetate and less than 250 mM acetate, or greater than 100 mM acetate and less than 200 mM acetate, or about 150 mM acetate. Preferably, the ionic strength of the buffering solution is around 50 mM acetate, 75 mM acetate, 100 mM acetate, 125 mM acetate, 150 mM acetate, 175 mM acetate, 200 mM acetate, 225 mM acetate, or 250 mM acetate. Any suitable acetate may be used, including lithium acetate, sodium acetate, and acetates of protonated organic amines such as tris-acetate, triethylamine, and piperidine.

Typically, the buffering solution contains an ionic detergent. Examples of such detergents include, without limitation, dodecyl sulfate (i.e., "SDS"), cetyltrimethyl ammonium bromide, lysolecithin, ether deoxylysolecithin, sodium cholate, sodium taurodeoxycholate, alkyl sulphonates, alkyl arylsulphonates, alkyl sulfates, alkyl arylsulfates, alkyl sarcosidates, cationic alkylamines, quaternary amines, and alkylpyridinium derivatives. Any soluble salt of the ionic detergent can be used, for example, sodium dodecyl sulfate. When present, the detergent is typically at a concentration between 0.05 weight percent and 0.25 weight percent. Oftentimes, it is present at a concentration between 0.075 weight percent and 0.2 weight percent, or at about 0.1 weight percent.

Oftentimes, the buffering solution contains a metal chelator. Typically, ethylenediaminetetraacetic acid is used, but any suitable metal chelator may be used. Metal chelator concentrations within the buffering solution are typically between 0.5 mM and 1.5 mM, 0.75 mM to 1.25 mM, or about 1 mM.

The step of collecting elution fractions typically includes observing an elution profile during size exclusion chromatography. When the polypeptide is exiting the column, its presence in an elution fraction is determined usually by observing the optical absorbance of the elution fractions at 280 nm. The absorbance values of each of the fractions are used to prepare an elution profile.

An asymmetry value of the elution profile is calculated. The asymmetry value is a ratio of a width from a tailing half of the peak to a width of a leading half of the peak measured at ten percent of peak height. Elution fractions containing the polypeptide are collected when the asymmetry value of the elution profile is between 0.4 and 1.6. Oftentimes elution fractions containing the polypeptide are collected when the asymmetry value of the elution profile is between 0.5 and 1.5, 0.6 and 1.4, 0.7 and 1.3, 0.8 and 1.2, or 0.9 and 1.1.

Methods of monitoring the presence of the polypeptide in an elution fraction include, without limitation, observing the absorbance of the elution fraction at $A_{280}$, conductivity measurements, and analysis by SDS-PAGE.

It typically takes less than 48 hours for the mixture comprising the polypeptide to pass through the column. Oftentimes, it takes less than 40, 35, 30, 25, 20, 15, 10, 5, or 3 hours.

In another method aspect of the invention, a method of commercializing a polypeptide is provided. The method involves identifying a polypeptide that can be used to treat a disease. The polypeptide is produced using either a natural or a synthetic route and then purified. Purification of the polypeptide involves using size exclusion chromatography involving a number of steps. A mixture comprising the polypeptide and a buffering solution is first prepared. The buffering solution includes greater than 50 mM acetate and less than 500 mM acetate. The mixture is passed through a column containing a polymeric gel, and fractions containing purified polypeptide and buffering solution are collected. Upon purification, the purified polypeptide is packaged, sold, and distributed.

The size exclusion chromatography step is performed according to the method described above for purifying a polypeptide.

DETAILED DESCRIPTION OF THE PREFERRED EMBODIMENTS

Figure 1:
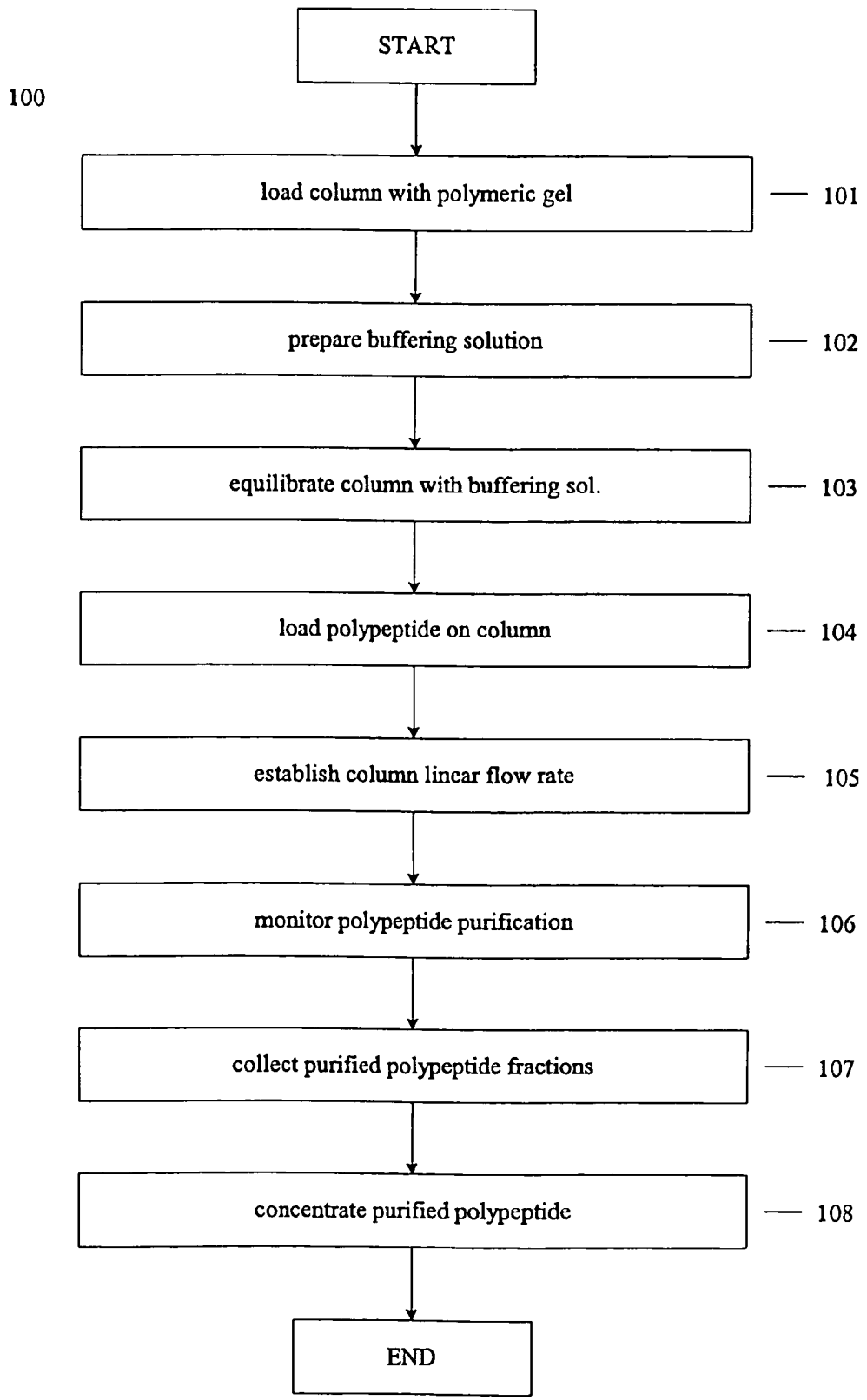
FIG. 1 illustrates a method of purifying polypeptides using the method of the present invention through use of a flow diagram.

The present invention is directed to the purification and commercialization of therapeutic polypeptides.

Definitions

"Acetate" refers to the anionic salt of acetic acid.

"Antibody" refers to a protein or proteins produced by certain white blood cells when exposed to foreign substances.

"Buffering Solution" refers to an aqueous solution at a defined pH.

"Column" refers to a housing for solid supports used in chromatography. Columns are typically cylindrical and are oriented in a vertical, upright position.

"Commercializing" refers to developing a business or business model involving sales and distribution of a particular product.

"Detergent" refers to a compound that has a nonpolar, hydrophobic part and a polar, hydrophilic part. Examples of ionic detergents include, without limitation, sodium dodecyl sulfate (i.e., "SDS"), cetyltrimethyl ammonium bromide, lysolecithin, ether deoxylysolecithin, sodium cholate, sodium taurodeoxycholate, alkyl sulphonates, alkyl arylsulphonates, alkyl sulfates, alkyl arylsulfates, alkyl sarcosidates, cationic alkylamines, quaternary amines, and alkylpyridinium derivatives.

"Dry Particle Diameter" refers to the range of polymeric gel diameters in the absence of a buffering solution.

"Elution Profile" refers to a graph made to show how much material is being carried out of a column by the buffering solution during size exclusion chromatography over time. The graph may show a number of different peaks; each peak represents a different separated material from the original mixed substance.

"Epoietin-α" refers to a 165 amino acid polypeptide that has the same biological effects as erythropoietin. It is sold under the tradename of EPOGEN®.

"Filgrastim" refers to a human granulocyte colony-stimulating factor (G-CSF). It is sold under the tradename of NEUPOGEN®.

"Interferon" refers to any of several polypeptides that help the body fight off viral infections. During a viral invasion, infected cells produce three kinds of interferon—α, β, and γ—that circulate in the blood stream and help make uninfected cells immune to the attack.

"Interferon β-1$_b$" refers to an interferon having 165 amino acids and an approximate molecular weight of 18,500 daltons. It is typically manufactured by cell fermentation or tissue culture from a genetically engineered plasmid containing the gene for human interferon beta$_{ser17}$.

"Interleukin" refers to any of a group of protein factors that are produced by T lymphocytes and macrophages in the presence of antigens or mitogens. They cause the T lymphocytes to activate and proliferate.

"Interleukin-2" refers to a protein factor that is producted by T lymphocytes that have been activated by an antigen. Interleukin-2 stimulates other T lymphocytes to activate and differentiate regardless of what specific antigen is involved. Interleukin-2 is known to be involved in achieving T-cell-mediated immunity.

"Ionic strength," μ, is defined as:

$$\mu = (1/2) \Sigma (c_i * Z^2)$$

$c_i$ is the concentration of each ion in the solution and Z is the charge of each ion in the solution. As an example: a solution of 0.1 M Na$_2$SO$_4$ has an ionic strength of:

$$\mu = (1/2) \Sigma (c_{Na} * Z^2_{Na} + c_{SO4} * Z^2_{SO4}) = (1/2) \Sigma [(2*0.1) *1^2 + (0.1)*2)]$$

$$\mu = (1/2) \Sigma (0.2 + 0.4)$$

$$\mu = 0.3$$

In a buffer such as sodium acetate buffer, only the sodium acetate part contributes to the ionic strength because acetic acid has no charge (Z=0). At pH 5.5 and using the pKa=4.8 at 25° C. for acetic acid, we calculated that approximately 80% of the total acetate buffer concentration is present in its salt form. The table below indicates the ionic strength of the various concentrations of acetate buffers at pH 5.5.

| | Acetate Buffer (M) | | | | | |
|---|---|---|---|---|---|---|
| | 0.010 | 0.050 | 0.100 | 0.150 | 0.200 | 0.250 |
| μ | 0.008 | 0.042 | 0.083 | 0.125 | 0.167 | 0.208 |

"Metal Chelator" refers to an organic chemical that bonds with and removes free metal ions from solution. A non-limiting example of a metal chelator is ethylenediaminetetraacetic acid.

"Monoclonal Antibody" refers to an antibody produced by a single clone of B cells. Monoclonal antibodies consist of a population of identical antibody molecules all specific for a single antigenic determinant.

"Natural Route of Production" refers to the use of cellular machinery to produce a particular compound. An example of this form of production is the use of recombinant DNA techniques to form a genetically engineered plasmid that produces a target compound.

"Packaging" refers to placing a product in a container for presentation to a consumer.

"Peak" refers to a positive deflection from baseline in an elution profile.

"Peak Asymmetry" refers to a ratio of width from a tailing half of a peak to a width of a leading half of the peak measured at ten percent of peak height. Perfect asymmetry corresponds to a peak asymmetry value of 1.0.

"Polypeptide" refers to a chain of peptides or amino acids, wherein the chain is longer than 2 amino acids long.

"Polymeric Gel" refers to a polymer crosslinked such that a gel network is formed. Examples of suitable polymeric gels for size exclusion chromatography include, without limitation, dextran (i.e., SEPHADEX®), agarose (i.e., SEPHAROSE®), and polyacrylamide (i.e., SEPHACRYL®). Polymeric gels such as Sephadex G75 SF, a preferred polymeric gel, are commercially available from a variety of vendors.

"Protein" refers to a large molecule composed of one or more chains of amino acids in a specific order. The order is determined by a base sequence of nucleotides in a gene coding for the protein. Proteins are required for the structure, function, and regulation of the body's cells, tissues and organs, and each protein has a unique function. Examples of proteins include, without limitation, hormones, enzymes, and antibodies.

"Purified" refers to the increase in concentration of a first component in a mixture relative to other components in the mixture. Typically, after purification, the concentration of the first component in the mixture is increased to greater than 50 weight percent. Preferably, the concentration is increased to greater than 60, 70, 80, 90, 95, or 99 weight percent.

"SDS-PAGE" refers to a well know laboratory technique called sodium dodecyl sulfate polyacrylamide gel electrophoresis. The technique is typically an analytical method used to separate polypeptides.

"Selling and Distributing" refers to the commercial disposition of a product.

"Size Exclusion Chromatography" refers to a type of chromatography that uses porous particles to separate molecules of different sizes. It is often used to separate biological molecules and to determine molecular weights and molecular weight distributions of polymers. Molecules that are smaller than the pore size can enter the particles and therefore have a longer path and longer transit time (retention time) than larger molecules that cannot enter the particles.

"Synthetic Route of Production" refers to the production of a compound using chemical reactions conducted in vitro. An example would be the solid phase synthesis of a polypeptide using a resin.

General Polypeptide Purification

The method of the present invention, in one aspect, is used to purify polypeptides. Examples of polypeptides that can be purified include, without limitation, proteins such as monoclonal antibodies, interferons (e.g., IFN β, IFN β-1$_a$, and IFN β-1$_b$), interleukins (e.g., IL-2), Filgrastin, and Epoietin-α. The method is used to purify any desired amount of polypeptide, but amounts greater than 1.0 g, 2.5 g, 5.0 g, 10 g, 25 g, 50 g, 100 g, 150 g, 200 g, 250 g, or 300 g are typical.

This method provides purified polypeptide wherein the amount of a contaminating polypeptide (e.g., a host protein when the desired polypeptide is recombinantly produced) is present at a concentration of less than 1 μg per 1 mg of the desired polypeptide. Preferably, the amount of contaminating polypeptide is present at a concentration of less than 500 ng per 1 mg of the desired polypeptide, less than 250 ng per 1 mg of the desired polypeptide, 100 ng per 1 mg of the desired polypeptide, 75 ng per 1 mg of the desired polypeptide. Even more preferably, the amount of contaminating polypeptide is present at a concentration of less than 50 ng per 1 mg of the desired polypeptide, 25 ng per 1 mg of the desired polypeptide, and 10 ng per 1 mg of the desired polypeptide.

Size exclusion chromatography is the primary technique used in the subject method, which is described in relation to FIG. 1. Method 100 starts with the loading of a column (e.g., 2.6×90 cm or 2.6×50 cm) with a polymeric gel (100). The polymeric gel is of any suitable composition. Nonlimiting examples of polymeric gels include dextran (i.e., SEPHADEX®), agarose (i.e., SEPHAROSE®), and polyacrylamide (i.e., SEPHACRYL®). Sephadex G75 SF, which has a dry particle diameter of 10 to 40 μm, is one specific type of polymeric gel used.

A buffering solution with a pH between 5.0 and 6.0 is prepared at 102, which serves as the chromatography eluant. The solution typically includes greater than 75 mM acetate and less than 500 mM acetate. Suitable acetates include, without limitation, lithium acetate, sodium acetate, and acetates of protonated organic amines such as tris, triethylamine, and piperidine.

Optional components of the buffering system include an ionic detergent and a metal chelator. Nonlimiting examples of ionic detergents include sodium dodecyl sulfate (i.e., "SDS"), cetyltrimethyl ammonium bromide, lysolecithin, ether deoxylysolecithin, sodium cholate, sodium taurodeoxycholate, alkyl sulphonates, alkyl arylsulphonates, alkyl sulfates, alkyl arylsulfates, alkyl sarcosidates, cationic alkylamines, quaternary amines, and alkylpyridinium derivatives. The detergent, when used, is typically present in the buffering solution at a concentration between 0.05 weight percent and 0.25 weight percent. Any suitable metal chelator can be used, with ethylenediaminetetraacetic acid (i.e., "EDTA") being one example. The metal chelator is typically present in the buffering solution at a concentration between 0.5 mM and 1.5 mM.

At 103, the column is equilibrated with a buffering solution. The polypeptide, which is concentrated, is loaded on the column (104), and a suitable linear flow rate for the column is established at 105. Linear flow rates used for the size exclusion chromatograpy are oftentimes between 0.8 cm/hr and 5 cm/hr, with typical values being 1.1 cm/hr and 3.3 cm/hr.

The polypeptide purification is monitored (106) through observation of the column's elution profile. Peaks on the elution profile graph are identified as either the desired polypeptide or an impurity. Methods of monitoring the presence of the polypeptide include, without limitation, observing absorbance profiles of elution fractions at $A_{280}$, solution conductivity, and performing gels using an aliquot from the column eluant as compared with a standard, pure polypeptide sample.

Target polypeptide is collected from elution fractions when the elution profile exhibits an asymmetry value between 0.2 and 1.8. Oftentimes, the asymmetry value will be between 0.3 and 1.7, 0.4 and 1.6, 0.5 and 1.5, 0.6 and 1.4, 0.7 and 1.3, 0.8 and 1.2, or 0.9 and 0.1.

Elution fractions containing purified polypeptide in buffering solution are collected (107) over a particular period of time. The non-buffering solution components of the fractions usually contain at least 50 percent by weight of the target polypeptide. Oftentimes, however, the non-buffering solution components contain at least 60, 70, 80, 90, 95, or 99 percent by weight of the target polypeptide. Fractions are collected less than 48 hours after polypeptide is loaded on the size exclusion column. Oftentimes, fractions are collected less than 40, 35, 30, 25, 20, 15, 10, 5 or 3 hours after the polypeptide is loaded on the column.

At 108, the polypeptide is optionally concentrated from the fractions. Purified polypeptide is accordingly provided.

Interferon $\beta$-$1_b$ Purification

Figure 2:
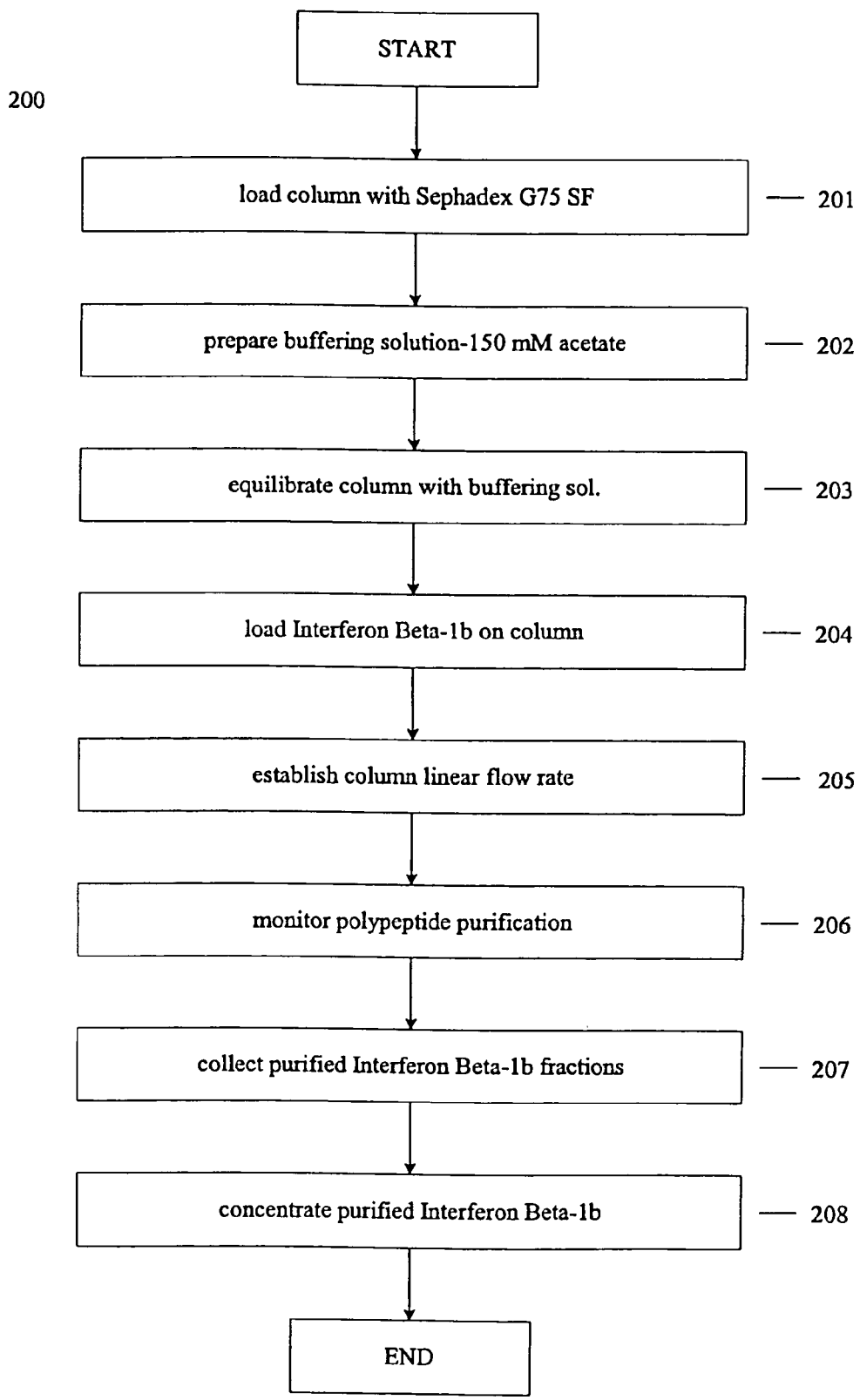
FIG. 2 illustrates a method of purifying Interferon β-$1_b$ using the method of the present invention through use of a flow diagram.

The method of the present invention, in another aspect, is used for the purification of Interferon $\beta$-$1_b$. Size exclusion chromatography as applied to IFN $\beta$-$1_b$ is described in relation to FIG. 2, which is directed to one embodiment.

Method 200 starts with the loading of a size exclusion chromatography column (e.g., 2.6×90 cm or 2.6×50 cm) with a polymeric gel of suitable composition (100). As shown, Sephadex G75 SF is loaded. The column volume containing the polymeric gel is typically less than 500 cm$^3$. Oftentimes the volume is less than 450 cm$^3$, 400 cm$^3$, 350 cm$^3$, or 300 cm$^3$. The method is used to purify any desired amount of Interferon $\beta$-$1_b$, but amounts greater than 1.0 g, 2.5 g, 5.0 g, 10 g, 25 g, 50 g, 100 g, 150 g, 200 g, 250 g, or 300 g are typical.

A buffering solution with a pH between 5.0 and 6.0 is prepared at 202, which serves as the chromatography eluant. Oftentimes, the pH of the buffering solution is between 5.2 and 5.8 or is about 5.5. The solution typically includes greater than 75 mM acetate and less than 500 mM acetate. Other suitable concentrations, include, without limitation, 100 mM to 225 mM, 100 mM to 200 mM, and about 150 mM. Step 202 shows the use of 150 mM acetate, which is oftentimes sodium acetate.

Optional components of the buffering system include an ionic detergent and a metal chelator. Sodium dodecyl sulfate (i.e., "SDS") is oftentimes chosen as the detergent and is typically included at a concentration between 0.05 weight percent and 0.25 weight percent. Other acceptable concentrations include, without limitation, 0.075 weight percent to 0.2 weight percent and about 0.1 weight percent. Ethylene-diamine-tetraacetic acid (i.e., "EDTA") is a commonly used metal chelator. EDTA concentrations in the buffering solution are oftentimes between 0.5 mM and 1.5 mM, with concentrations of 0.75 mM to 1.25 mM or about 1 mM being typical.

The column is equilibrated with a buffering solution at 203. Concentrated Interferon $\beta$-$1_b$ is loaded onto the column (204), ensuring that the load is generally not more than 1% of column volume. A column linear flow rate is established (205). Linear flow rates used for the size exclusion chromatograpy are oftentimes between 0.8 cm/hr and 5 cm/hr, with typical values being about 1.1 cm/hr and 3.3 cm/hr.

Interferon $\beta$-$1_b$ purification is monitored (206) through observation of the column's elution profile. Peaks on the elution profile graph are identified as either the Interferon $\beta$-$1_b$ or an impurity. Methods of monitoring the presence of Interferon $\beta$-$1_b$ in include, without limitation, observing the absorbance profiles of elution fraction at $A_{280}$, conductivity measurements, and analysis by SDS-PAGE. *E. Coli* protein contaminants can be quantified by ELISA (enzyme-linked immunosorbant assay).

Interferon $\beta$-$1_b$ is collected from elution fractions when the elution profile exhibits an asymmetry value between 0.2 and 1.8. Oftentimes, the asymmetry value will be between 0.3 and 1.7, 0.4 and 1.6, 0.5 and 1.5, 0.6 and 1.4, 0.7 and 1.3, 0.8 and 1.2, or 0.9 and 1.1. A peak corresponding to the Interferon $\beta$-$1_b$ exhibits an asymmetry value between 0.4 and 1.6. Oftentimes, the asymmetry value will be between 0.5 and 1.5, 0.6 and 1.4, 0.7 and 1.3, 0.8 and 1.2, or 0.9 and 1.1.

Purified Interferon $\beta$-$1_b$ fractions in buffering solution are collected (207) over a particular period of time. The non-buffering solution components of the fractions usually contain at least 70 percent by weight of the target polypeptide. Oftentimes, however, the non-buffering solution components contain at least 80, 90, 95, or 99 percent by weight of the target polypeptide. Fractions are collected less than 48 hours after polypeptide is loaded on the size exclusion column. Oftentimes, fractions are collected less than 40, 35, 30, 25, 20, 15, 10, 5, or 3 hours after the polypeptide is loaded on the column. Purified Interferon $\beta$-$1_b$ is optionally concentrated from the fractions at 208.

Figure 3:
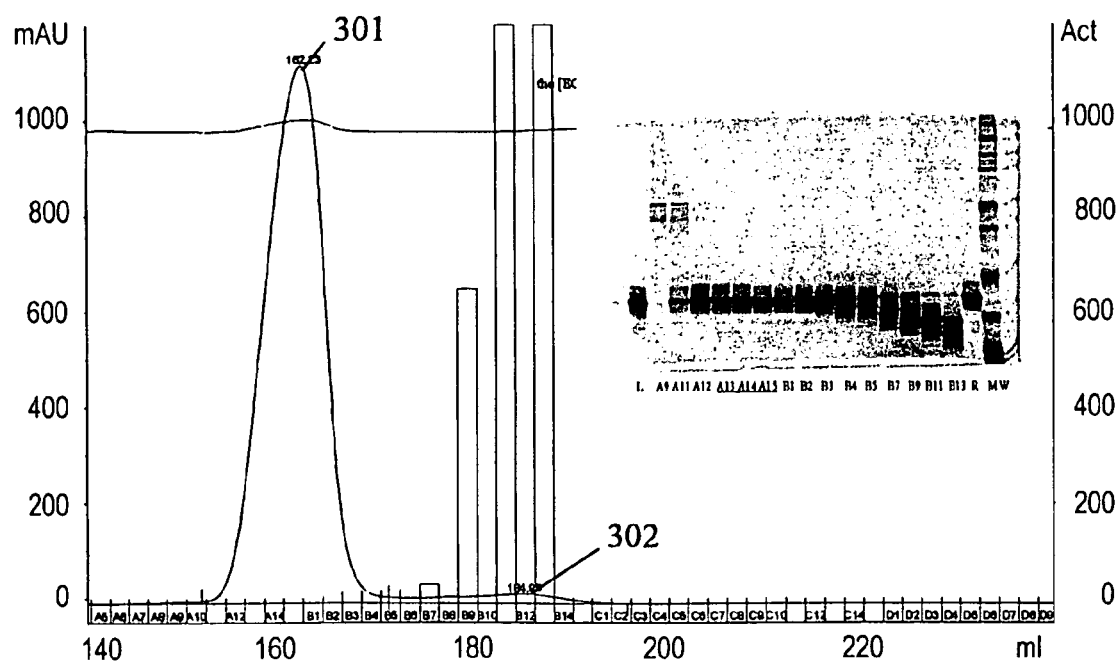
FIG. 3 illustrates a chromatogram and SDS-PAGE of Interferon β-$1_b$ separation using a 90 cm Sephadex G-75 column with a buffering solution containing 150 mM sodium acetate and 0.1% SDS. The horizontal line shows the conductivity measurements of the elution fractions. The histogram shows the elution fractions where the impurities elute from the column.
Figure 4:
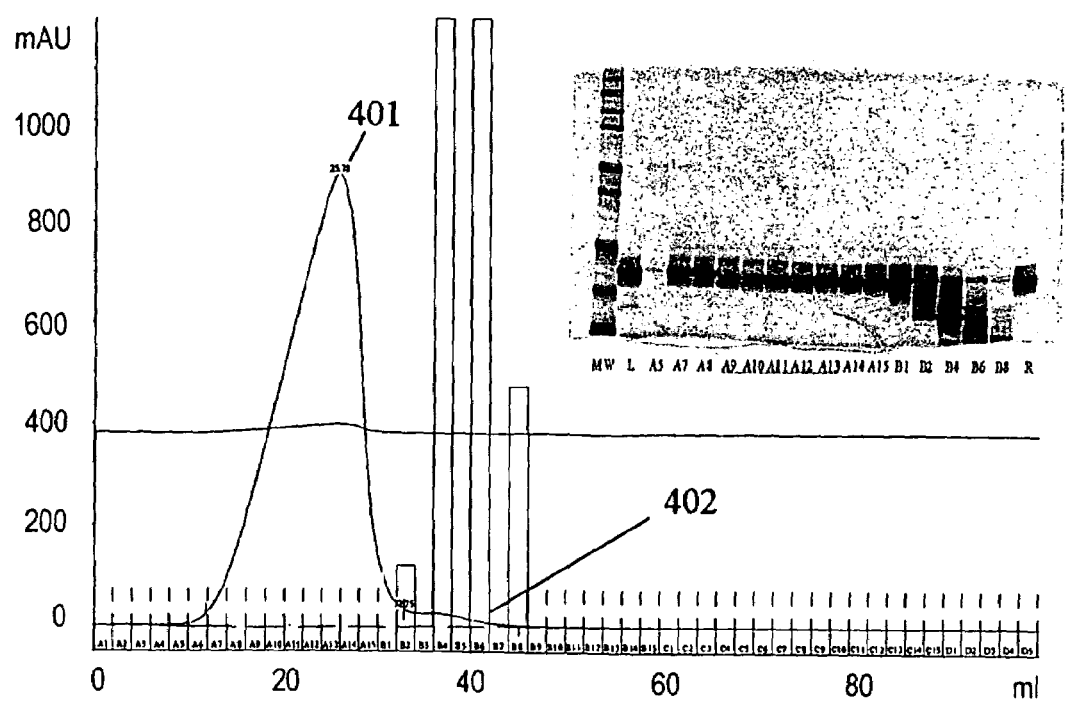
FIG. 4 illustrates a chromatogram and SDS-PAGE of Interferon β-1$_b$ separation using a 90 cm Sephadex G-75 column with a buffering solution containing 50 mM sodium acetate and 0.1% SDS. The horizontal line shows the conductivity measurements of the elution fractions. The histogram shows the elution fractions where the impurities elute from the column.

FIG. 3 illustrates a chromatogram and an SDS-PAGE of Interferon $\beta$-$1_b$ separation using a 90 cm Sephadex G-75 column with a buffering solution containing 150 mM sodium acetate and 0.1% SDS. A comparison with FIG. 4 (50 mM sodium acetate) shows how a change in acetate concentration can affect Interferon $\beta$-$1_b$ purification. Peak 301 of FIG. 3, which corresponds to Interferon $\beta$-$1_b$, is clearly resolved from broad peak 302, which represents *E. Coli* contaminants. Peak 402 of FIG. 4, which also corresponds to *E. Coli* contaminants, however, merges with Interferon $\beta$-$1_b$ peak 401. In other words, the separation (i.e., purification) shown in FIG. 4 is significantly worse than that shown in FIG. 3.

Figure 5:
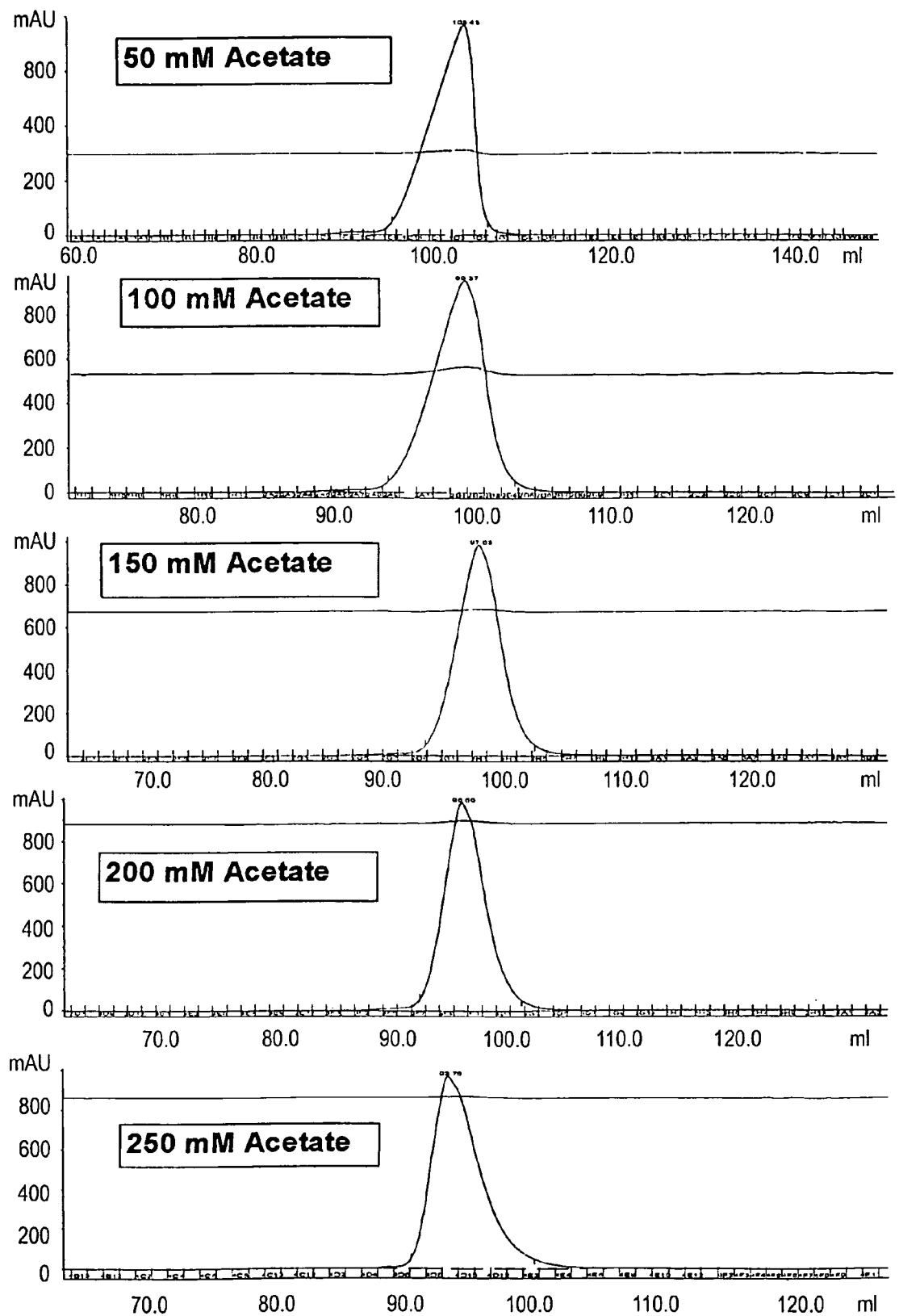
FIG. 5 illustrates several chromatograms of Interferon β-1$_b$ separation using a 50 cm Sephadex G-75 column with a buffering solution containing five different concentrations of sodium acetate (50 mM, 100 mM, 150 mM, 200 mM and 250 mM) at a linear flow rate of 1.1 cm/hr.

The effect of acetate concentration on Interferon $\beta$-$1_b$ resolution is further seen in reference to FIG. 5. This figure shows size exclusion chromatography elution profiles of pure Interferon $\beta$-$1_b$ at 5 different acetate concentrations. Proceeding from 50 mM acetate to 100 mM acetate, one sees that the exhibited peak becomes more symmetrical. Peak symmetry, which typically corresponds with compound resolution, becomes even better at 150 mM and then declines as higher acetate concentrations are employed (200 mM and 250 mM).

Tables 1 and 2 show studies comparing Interferon $\beta$-1b peak asymmetry to sodium acetate concentration at two different flow rates. The values in table 1 were measured using Unicorn 4.10, a commercially available chromatography system from GE Healthcare.

TABLE 1 column height 49 cm; column $V_0$ 86.7 ml; flow 1.1 cm/hr.

| | Na Acetate (mM) | | | | |
|---|---|---|---|---|---|
| | 50 | 100 | 150 | 200 | 250 |
| Retention (ml) | 103 | 99 | 98 | 97 | 94 |
| Peak Width at half height (ml) | 5.4 | 4.2 | 4.0 | 3.9 | 4.0 |
| $K_{av}$ | 0.096 | 0.073 | 0.063 | 0.057 | 0.041 |
| Asymmetry Value | 0.31 | 0.62 | 0.97 | 1.32 | 2.07 |

TABLE 2 column height 49 cm; column $V_0$ 86.7 ml; flow 3.3 cm/hr.

| | Na Acetate (mM) | | | | |
|---|---|---|---|---|---|
| | 50 | 100 | 150 | 200 | 250 |
| Retention (ml) | 103 | 100 | 98 | 97 | 95 |
| Peak Width at half height (ml) | 6.2 | 4.9 | 4.8 | 4.8 | 4.8 |
| $K_{av}$ | 0.096 | 0.075 | 0.063 | 0.057 | 0.047 |
| Asymmetry Value | 0.46 | 0.87 | 1.31 | 1.64 | 2.33 |

Polypeptide Commercialization

Figure 6:
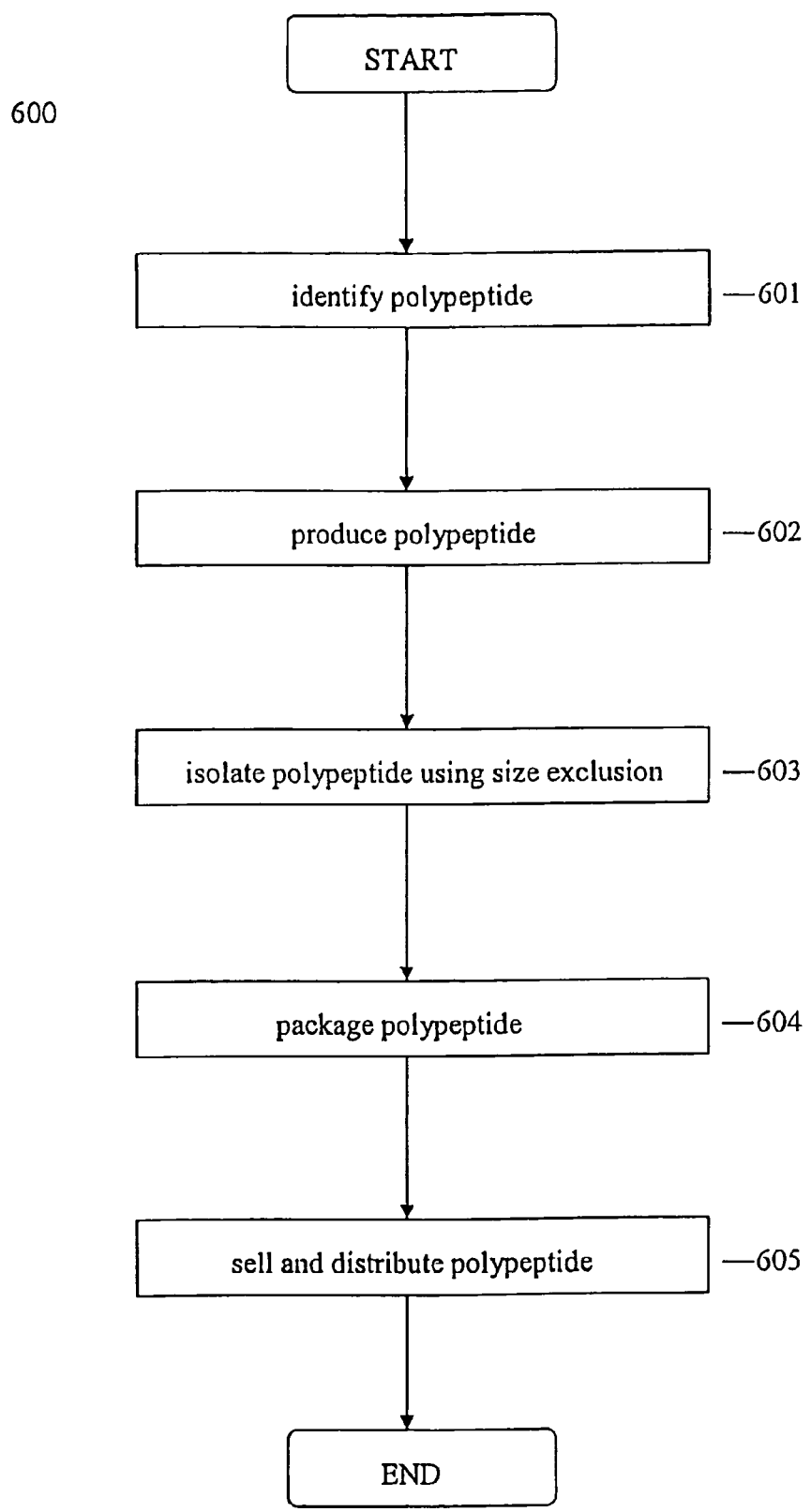
FIG. 6 illustrates a method of commercializing a polypeptide as outlined in a flow diagram.
Figure 7:
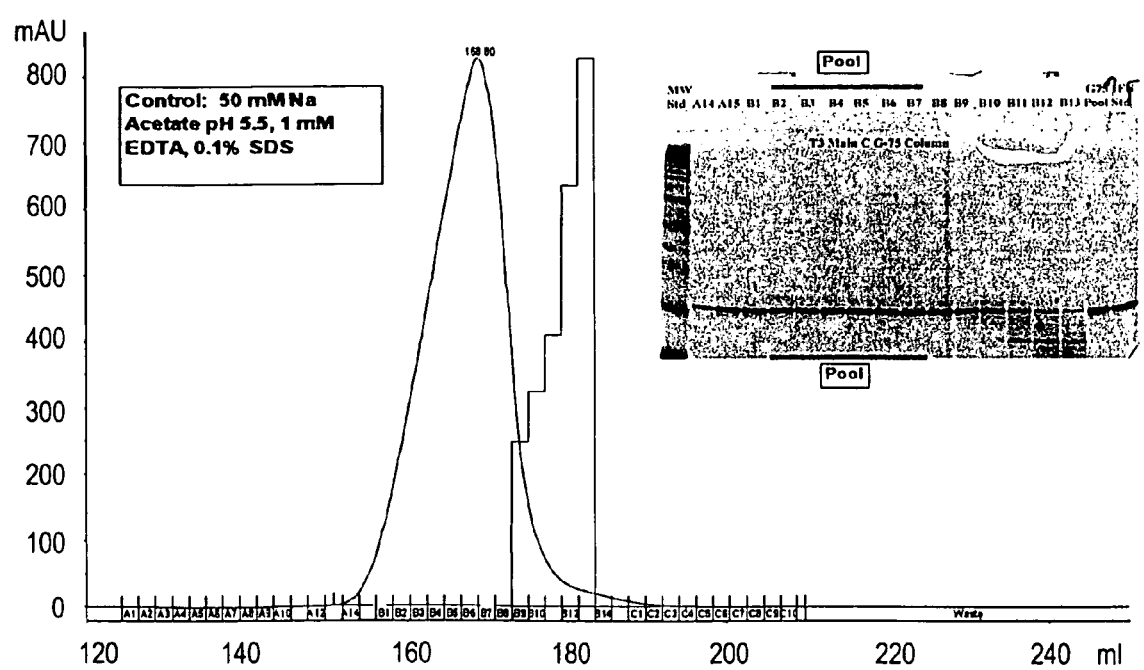
FIG. 7 illustrates a chromatogram and SDS-PAGE of Interferon β-1$_b$ separation from *E. Coli* proteins using a 90 cm Sephadex G-75 column with a buffering solution containing 50 mM sodium acetate and 0.1% SDS. The horizontal line shows the conductivity measurements of the elution fractions. The histogram shows the elution fractions where the impurities elute from the column.
Figure 8:
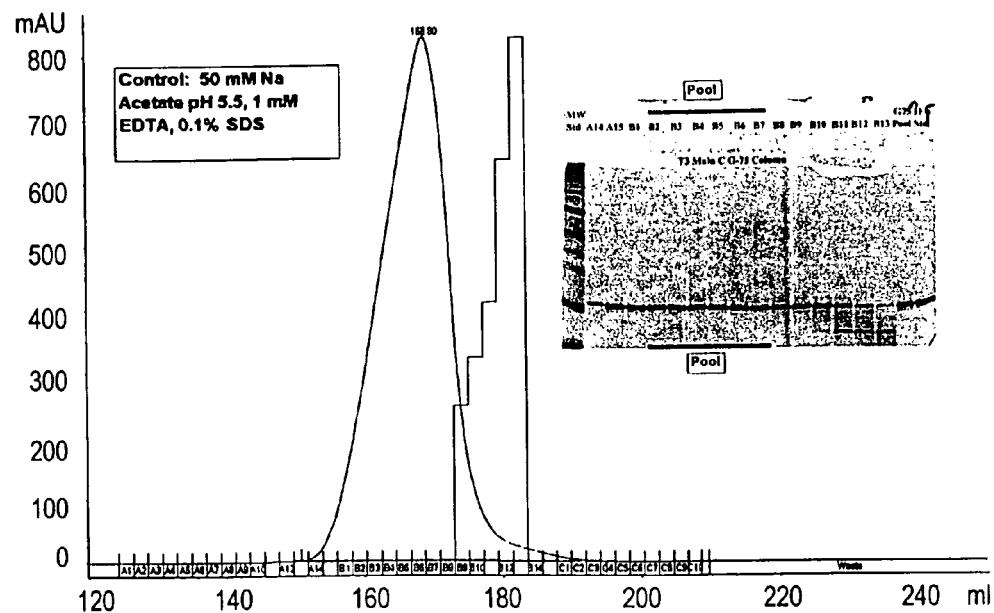
FIG. 8 illustrates two chromatograms of Interferon β-1$_b$ separation. The top chromatogram shows the use of a 90 cm Sephadex G-75 column with a buffering solution containing 50 mM sodium acetate and 0.1% SDS. The bottom chromatogram shows the use of a 90 cm Sephadex G-75 column with a buffering solution containing 10 mM sodium acetate and 0.1% SDS.
Figure 8:
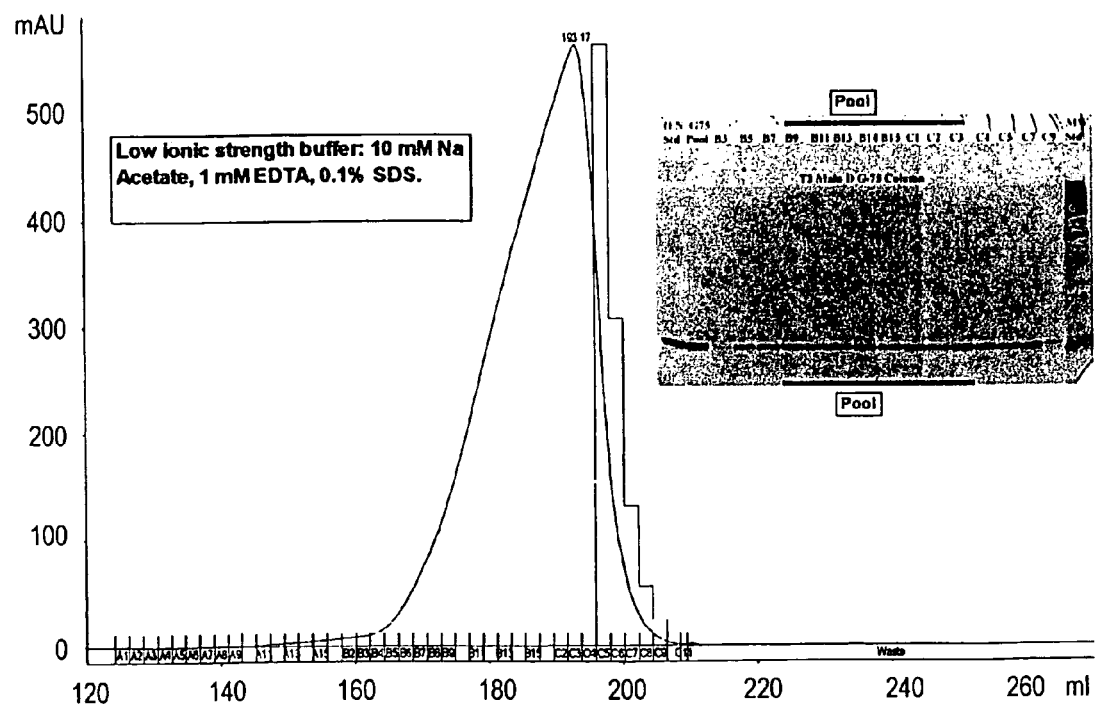
Figure 9:
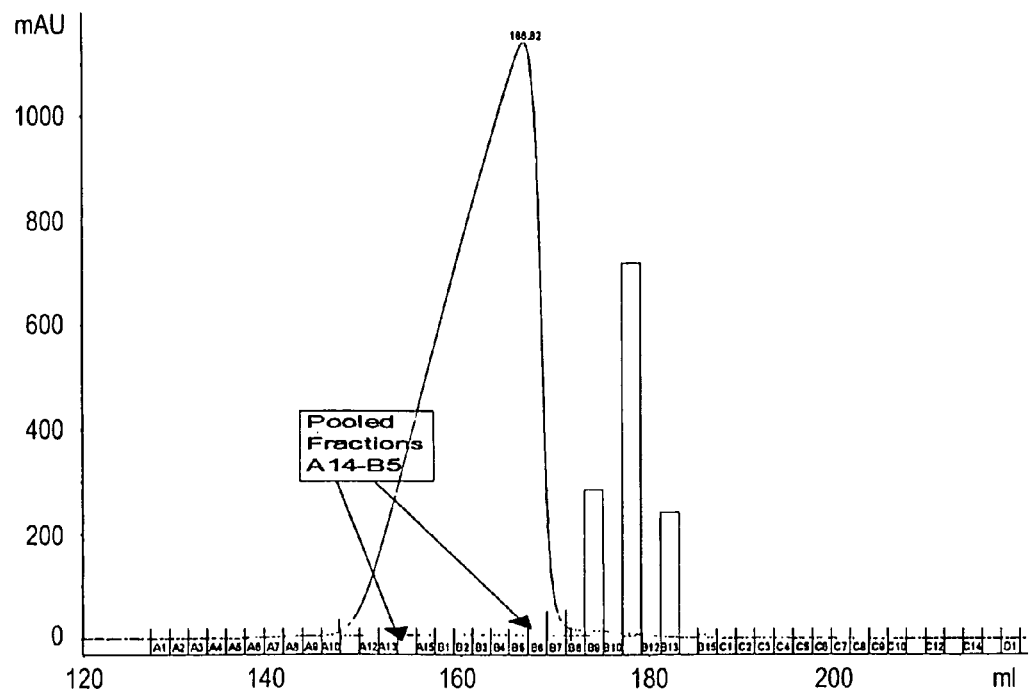
FIG. 9 illustrates two chromatograms of Interferon β-1$_b$ separation. The top chromatogram shows the use of a buffering solution containing 50 mM sodium acetate, 1 mM EDTA, and 0.1% SDS at a pH of 5.5. The bottom chromatogram shows the use of a buffering solution containing 10 mM sodium acetate, 1 mM EDTA, and 0.25% SDS at a pH of 5.5.
Figure 9:
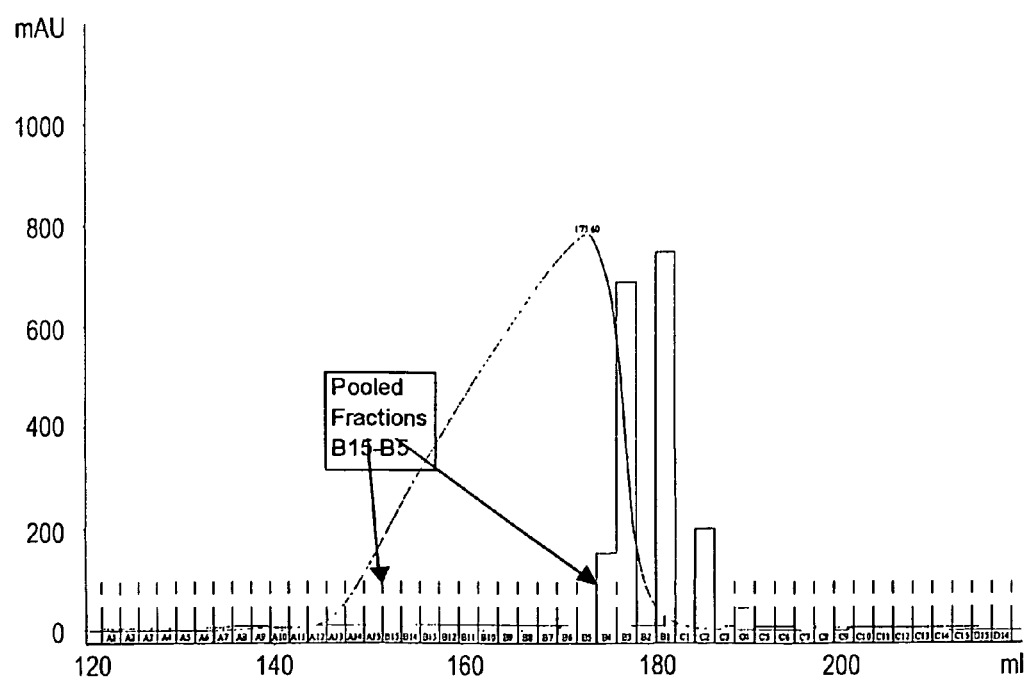
Figure 10:
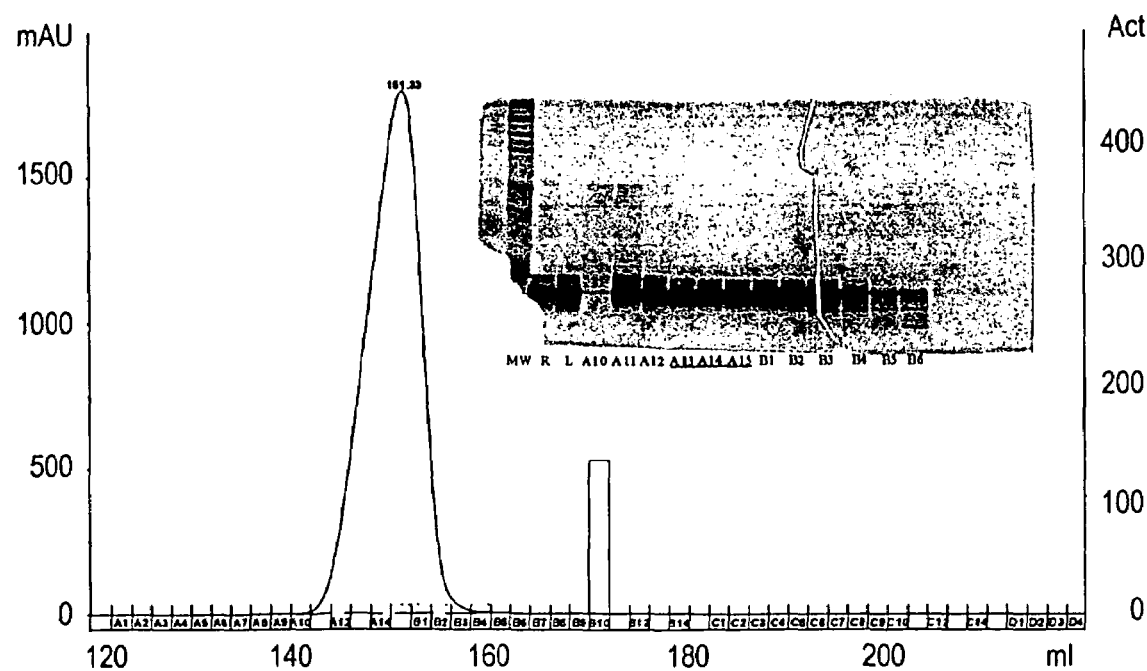
FIG. 10 illustrates two chromatograms of Interferon β-1$_b$ separation. The top chromatogram shows the use of a 90 cm Sephadex G-75 column with a buffering solution containing 150 mM sodium acetate, 1 mM EDTA, and 0.1% SDS at pH 5.5. The bottom chromatogram shows the use of a 50 cm Sephadex G-75 column with a buffering solution containing 150 mM sodium acetate, 1 mM EDTA, and 0.1% SDS at pH 5.5.
Figure 10:
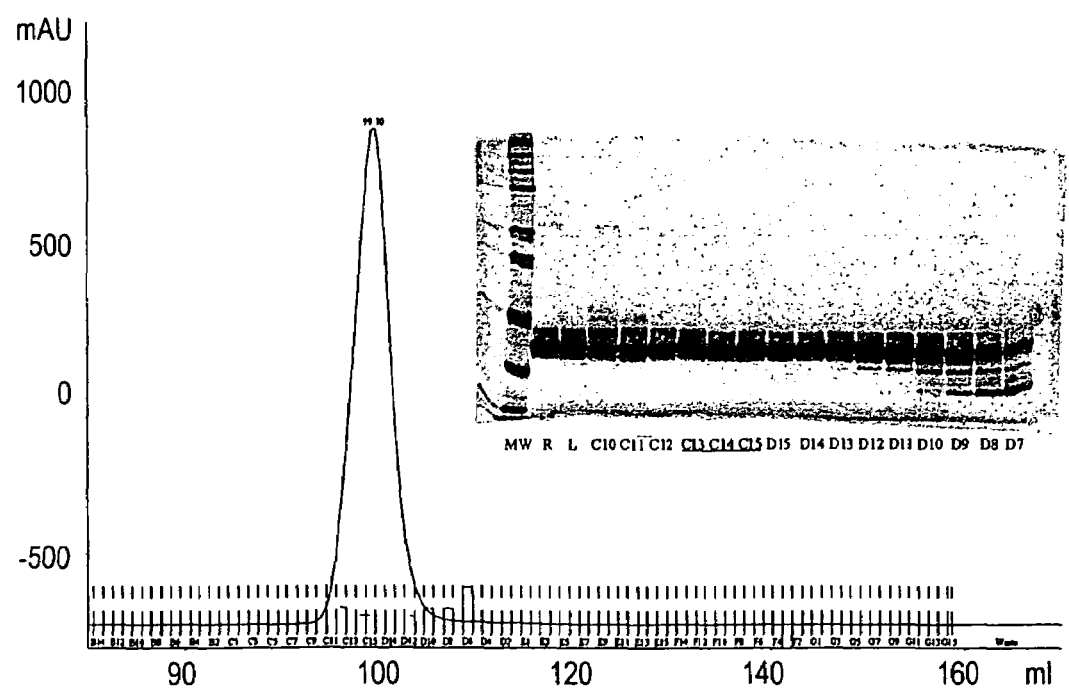
Figure 11:
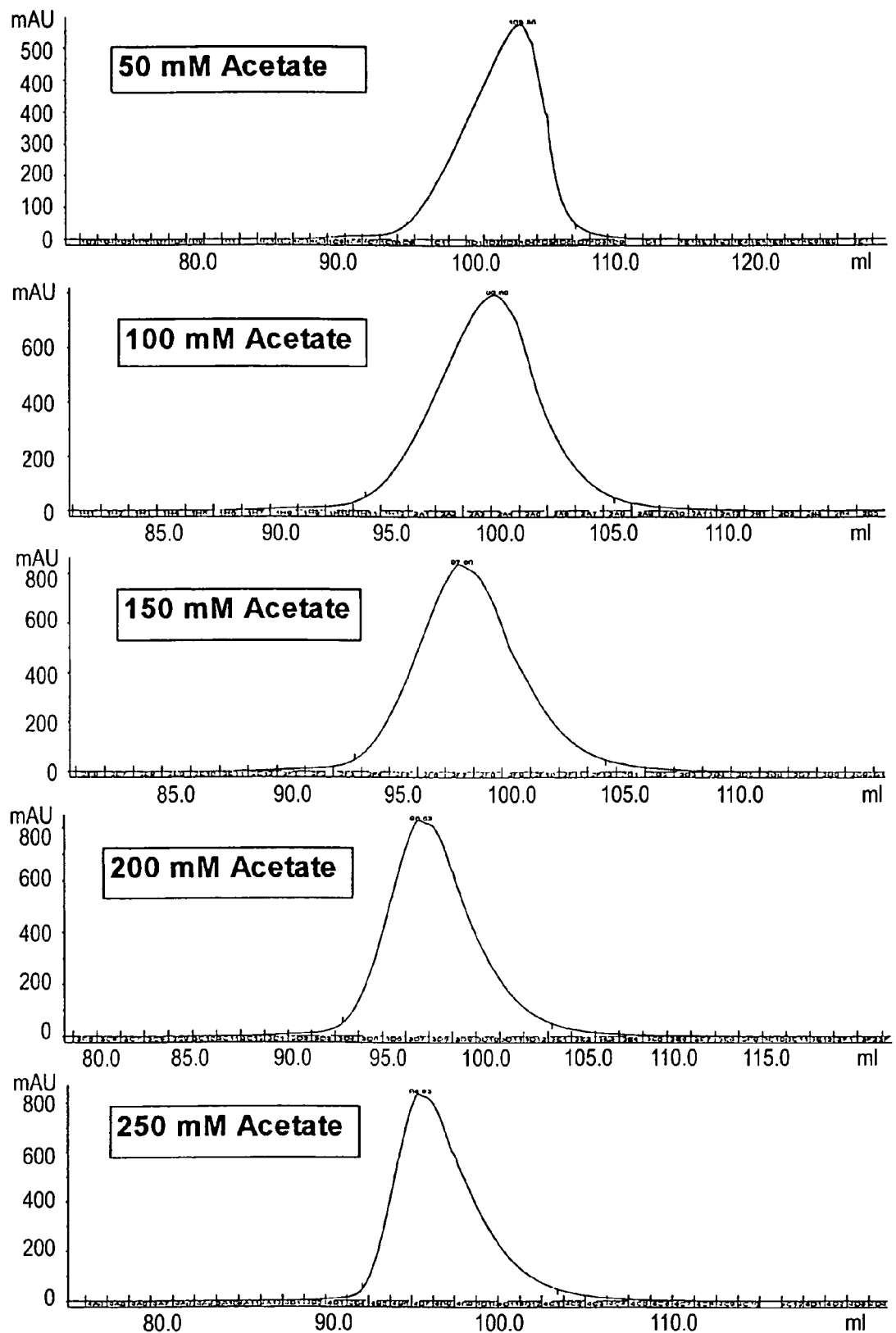
FIG. 11 illustrates illustrates several chromatograms of Interferon β-1$_b$ separation using a 50 cm Sephadex G-75 column with a buffering solution containing five different concentrations of sodium acetate (50 mM, 100 mM, 150 mM, 200 mM and 250 mM) at a linear flow rate of 3.3 cm/hr.

The method of the present invention, in another aspect, relates to commercializing a polypeptide. This aspect is described in relation to FIG. 6.

Method 600 begins with identifying a polypeptide that can be used to treat a disease at 601. Examples of such polypeptides include, without limitation, monoclonal antibodies, interferons (e.g., IFN p, IFN β-1a, and IFN β-1b), interleukins (e.g., IL-2), Filgrastin, and Epoietin-α. Any suitable method can be used to identify the polypeptide. Such a method, however, will oftentimes include an analysis of U.S. or European sales data for a particular polypeptide or a market forecast that predicts future sales.

At 602, the polypeptide is produced. Production is carried out using either a natural or synthetic route. Size exclusion chromatography is used to isolate the polypeptide. Suitable methods of size exclusion chromatography used in step 602 include the methods described above in the sections entitled General Polypeptide Purification and Interferon β-1$_b$ Purification.

The polypeptide is packaged at 604 in a container for presentation to a consumer. Examples of consumers include, without limitation, managed care groups, nursing facilities, physicians and patients. Sale and distribution of the packaged product is performed at 605.

In order that the invention and its advantages may be more completely understood, the following examples are provided as a means of illustration but are in no way considered as a limitation on the scope of the present invention.

Experimental Section

EXAMPLE 1

General Method for Size Exclusion Chromatography of Polypeptides

A column (e.g., 2.6×90 cm or 2.6×50 cm) is packed with an appropriate polymeric gel. Column equilibration is performed with a buffering solution. The buffering solution is an aqueous solution typically containing 75 to 250 mM sodium acetate, 0.1% SDS, and 1 mM ethylenediaminetetraacetic acid at pH 5.5. The column is loaded with concentrated polypeptide (e.g., Interferon β-1, monoclonal antibody, interleukin-2, Filgrastim, Epoietin-α), making sure the load is not more than 1% of column volume. Linear flow rate for load and elution of the polypeptide is set at about 1 cm/hr. The chromatographic separation is followed by the UV-VIS spectroscoapy at $A_{280}$ or conductivity. Selected fractions are analyzed by SDS-PAGE in 15% gels (Criterion, Bio-Rad) with silver staining and the *E. Coli* protein contaminants quantified by ELISA (courtesy of QC). Elution fractions are collected and concentrated to provide purified polypeptide.

EXAMPLE 2

Purification of Interferon β-1$_b$ Using Size Exclusion Chromatography

The following procedures were performed at room temperature. A 2.6×50 cm or a 2.6×90 cm column was packed with Sephadex G75 SF. Column equilibration was performed with an aqueous buffering solution at pH 5.5 containing the following components: 10 mM, 50 mM, 100 mM, 150 mM, 200 mM, or 250 mM sodium acetate. The buffering solutions also comprised 0.1% SDS, or 0.25% SDS and 1 mM ethylenediaminetetraacetic acid. The columns were loaded with concentrated Interferon β-1$_b$, making sure the load was not more than 1% of column volume. Linear flow rate for load and elution of the polypeptide was set at about 1 cm/hr or 3.3 cm/hr. Chromatographic separation was observed by the polypeptide's absorbance at $A_{280}$ and conductivity. Selected fractions were analyzed by SDS-PAGE in 15% gels (Criterion, Bio-Rad) with silver staining and the *E. Coli* protein contaminants quantified by ELISA (courtesy of QC). Pure fractions were collected and concentrated to provide purified polypeptide.

The purification results are shown in FIGS. 7-11.

EXAMPLE 3

Discussion of Effect of Ionic Strength on Size Exclusion Chromatography in the Presence of Detergents At low concentrations ionic detergents exist as monomers, until the concentration reaches a value known as the Critical Micelle Concentration (CMC) where the monomers coexist with an aggregated form of detergent known as micelles (Helenius et. al. 1979). The CMC is defined as the maximum monomer concentration that can coexist with micelles. The following equation describes the behavior of monomer and micelles:

Micelles<=>Monomer

This equation is not a true chemical equilibrium equation; if the total concentration of detergent is increased above the CMC, the amount of Monomer detergent remains the same (CMC) but the amount of detergent in Micelles increases.

Micelles in aqueous solutions are normally structures with the hydrophobic tail of the detergent monomer interacting with the hydrophobic tail of other monomers forming a structure like an oil drop. The ionic moiety of the detergent is orientated to the outside phase of this oil micro drop, interacting with the aqueous solvent and protecting the hydrophobic moiety of the micelle from the aqueous phase. The repulsion of the charges of the ionic moiety of the detergent limits the stability and the size of the micelle.

The number of monomer ionic detergent molecules per micelle, and therefore, the size of the ionic micelles, is a function of the ionic strength.

Increasing the ionic strength of the solution in contact with the micelles decreases the charge repulsion between the ionic moieties of the detergent molecules in the micelles producing a stabilization of the micelles. An increase in the ionic strength increases the number of detergent monomer in a micelle and therefore increases the size of the micelle. In addition, the CMC decreases with increasing the ionic strength.

When a protein is exposed to ionic detergents the following equation applies:

Micelles<=>Monomer+Protein<=>Protein-Micelles

A model of binding of ionic detergents to proteins has been established with a model protein like BSA and a model detergent such as SDS (Turro et. al. 1995). The binding of monomeric SDS to protein can be described in stages. In the initial detergent-binding phase, a small number of detergent molecules bind with very high affinity to selected sites in the protein. In the unfolding phase, there is a cooperative binding of SDS monomers to protein exposing new detergent binding sites. And finally a protein saturating phase, where the protein reaches the maximum binding of detergent. Starting in the unfoldng phase the SDS molecules start aggregating, creating mini-micelles, again with the charged detergent moiety facing the outside phase, and the hydrophobic tails interacting with each other creating again a micro oil drop. The protein wraps around the charged mini-micelles creating a "necklace and bead structure".

Effect of Ionic Strength on Protein-(Mini-Micelles)$_x$

We observed an apparent continuous increase in the size of the IFN-SDS complex with the increase of acetate concentration during Sephadex G75 SF chromatography in the presence of 0.1% SDS. The apparent size increase of the IFN-SDS complex was detected by the decrease in the IFN Kav parameter with the increase of acetate concentration.

Before the definition of Kav is provided, the different phases in a gel filtration column is discussed. The column total volume (Vt) is the sum of the volume of the resin beads (Vb) plus the volume between the beads (Vo or Void Volume); the volume of the resin beads is the sum of the resin internal volume (Vi) plus the volume of the gel (Vg). The Vo is a constant in Sephadex resins of 30% of Vt. Therefore, the Vt is defined as:

$$V_t = V_o + V_b = V_o + V_i + V_g$$

The $K_{av}$ is defined as:

$$K_{av} = (V_e - V_o)/(V_t - V_o)$$

Ve is the elution Volume of IFN-SDS complex.

The term (Ve−Vo) is a measurement of how much of the resin internal volume is accessible to the IFN-SDS complex; if the complex is too big to penetrate the resin pores the complex will elute in the Vo (Ve=VO) and the Kav=0.

The term (Vt−Vo) is the total resin bead volume, therefore Kav is a ratio of how much the molecule can partition to the internal volume of the beads. The bigger the molecule the smaller is the Kav.

There are two proposed mechanism for the observed effect of ionic strength on the Kav and elution volume (Ve) of IFN-SDS complex in size exclusion chromatography.

Increase in size of SDS micelle. The size of ionic detergent micelles increases with the ionic strength as described above. The bigger micelles could fill more volume in the internal volume of the resin bead ($V_i$), therefore it could decrease the bed internal volume available to the Protein-SDS complex. The net effect on the Protein-SDS complex would result in smaller elution volume ($V_e$) and a decrease in the partition of the Protein-SDS complex inside of the bed (decrease of $K_{av}$). 1B) It is possible that the high density of negative charges in SDS micelles could produce electrostatic repulsion of the negative charges in the Protein-SDS, contributing to the decrease of the available internal volume of the resin bead ($V_i$), decreasing the elution volume ($V_e$) and a decrease in the partition of the Protein-SDS complex inside of the bed (decrease of $K_{av}$).

Protein-SDS complex size expansion at higher ionic strength. The higher ionic strength could also increase the size of SDS mini-micelles attached to the protein by increasing the number of SDS molecules in the mini-micelles. The increase in size of mini-micelles attached to the protein could produce size expansion of the Protein-SDS complex resulting in smaller elution volume ($V_e$) and a decrease in the partition of the Protein-SDS complex inside of the resin bead (decrease of $K_{av}$).

Finally, it is possible that the chromatographic effects observed are the result of combination of mechanisms one and two.

It is also possible that the big changes in the elution properties of IFN-SDS complexes with ionic strength in Sephadex G75 SF is due to its small $K_{av}$ (0.096 at 50 mM acetate). The IFN-SDS complex barely partitions into the resin bead inner volume ($V_i$), therefore small changes in its size has a more dramatic effect than smaller proteins that partition more readily into the resin bead inner volume ($V_i$).

What is claimed is:

1. A method of purifying an interferon by size exclusion chromatography comprising the steps of:
    preparing a buffering solution having an ionic strength of greater than 50 mM and less than 500 mM, said buffering solution further comprising an ionic detergent wherein the ionic detergent is sodium dodecylsulfate (SDS);
    loading a size exclusion chromatography column with said interferon
    eluting said interferon with the buffering solution from the size exclusion chromatography column;
    observing an elution profile and determining an asymmetry value of the elution profile; and
    collecting elution fractions when the asymmetry value of the elution profile is between 0.4 and 1.5.

2. The method of claim 1 wherein said buffering solution has an ionic strength of greater than 75 mM and less than 250 mM.

3. The method of claim 1 wherein said buffering solution has an ionic strength of greater than 100 mM and less than 200 mM.

4. The method of claim 1 wherein said buffering solution has an ionic strength of about 100 mM.

5. The method of claim 1 wherein said buffering solution has an ionic strength of about 150 mM.

6. The method of claim 1 wherein said buffering solution has an ionic strength of about 200 mM.

7. The method of claim 1 wherein said buffering solution comprises sodium acetate.

8. The method of claim 1 wherein said ionic detergent is present in the buffering solution at a concentration of between 0.05 weight percent and 0.25 weight percent.

9. The method of claim 1 wherein said ionic detergent is present in the buffering solution at a concentration of between 0.075 weight percent and 0.2 weight percent.

10. The method of claim 1 wherein said ionic detergent is present in the buffering solution at a concentration of about 0.1 weight percent.

11. The method of claim 1 wherein said buffering solution further comprises a metal chelator.

12. The method of claim 11 wherein said metal chelator is ethylenediamine-tetraacetic acid.

13. The method of claim 11 wherein said metal chelator is present at a concentration of between 0.5 mM to 1.5 mM.

14. The method of claim 11 wherein said metal chelator is present at a concentration of about 1 mM.

15. A method of purifying an interferon by size exclusion chromatography comprising the steps of:
   preparing a buffering solution having an ionic strength of greater than 50 mM and less than 500 mM, said buffering solution further comprising an ionic detergent wherein the ionic detergent is sodium dodecylsulfate (SDS) at a concentration of between 0.05 weight percent and 0.25 weight percent;
   loading a size exclusion chromatography column with said interferon;
   eluting said interferon with buffering solution from the size exclusion chromatography column;
   observing an elution profile and determining an asymmetry value of the elution profile; and
   collecting elution fractions when the asymmetry value of the elution profile is between 0.4 and 1.6.

16. The method of claim 15 wherein said buffering solution has an ionic strength of greater than 75 mM and less than 250 mM and the ionic detergent is at a concentration of between 0.075 weight percent and 0.2 weight percent.

17. The method of claim 15 wherein said buffering solution has an ionic strength of greater than 100 mM and less than 200 mM and the ionic detergent is at a concentration of about 0.1 weight percent.

18. The method of claim 15 wherein said buffering solution has an ionic strength of about 150 mM and the ionic detergent is at a concentration of about 0.1 weight percent.

19. The method of claim 15 wherein the asymmetry value of the elution profile is between 0.5 and 1.5.

20. The method of claim 15 wherein the asymmetry value of the elution profile is between 0.6 and 1.4.

21. The method of claim 15 wherein the asymmetry value of the elution profile is between 0.8 and 1.2.

22. The method of claim 15 wherein the asymmetry value of the elution profile is between 0.9 and 1.1.

23. A method of purifying an interferon by size exclusion chromatography comprising the steps of:
   preparing a buffering solution having an ionic strength of greater than 50 mM and less than 500 mM, said buffering solution further comprising an ionic detergent wherein the ionic detergent is sodium dodecylsulfate (SDS) at a concentration of between 0.05 weight percent and 0.25 weight percent and a metal chelator at a concentration of between 0.5 and 1.5 mM;
   loading a size exclusion chromatography column with said interferon;
   eluting said interferon with buffering solution from the size exclusion chromatography column;
   observing an elution profile and determining an asymmetry value of the elution profile; and
   collecting elution fractions when the asymmetry value of the elution profile is between 0.4 and 1.6.

24. The method of claim 23 wherein said metal chelator is ethylenediamine-tetraacetic acid.

25. The method of claim 23 wherein the buffering solution has an ionic strength of greater than 50 mM and less than 500 mM, said buffering solution further comprising an ionic detergent at a concentration of between 0.05 weight percent and 0.25 weight percent and a metal chelator at a concentration of about 1 mM.

26. The method of claim 23 wherein the buffering solution has an ionic strength of about 150 mM, said buffering solution further comprising an ionic detergent at a concentration of about 0.1 weight percent and a metal chelator at a concentration of about 1 mM.

27. The method of claim 26 wherein the asymmetry value of the elution profile is between 0.6 and 1.4.

28. The method of claim 26 wherein the asymmetry value of the elution profile is between 0.8 and 12.

29. The method of claim 26 wherein the asymmetry value of the elution profile is between 0.9 and 1.1.

30. The method of claim 1 wherein said interferon is interferon-β.

31. The method of claim 30 wherein said interferon is interferon-$β_b$.

32. The method of claim 1 wherein the amount of the interferon purified is greater than 1 gram.

* * * * *